United States Patent [19]

Siciliano

[11] Patent Number: 5,078,709

[45] Date of Patent: Jan. 7, 1992

[54] EVAPORATING ATTACHMENT MEANS SUITABLE FOR CONTAINING AND DRAINING FLUIDS EMANATING FROM A SUBJECT

[75] Inventor: Anthony A. Siciliano, Ardsley, N.Y.

[73] Assignee: Evaporating Apparel Industries, Saddle River, N.J.

[21] Appl. No.: 593,997

[22] Filed: Oct. 9, 1990

Related U.S. Application Data

[63] Continuation-in-part of Ser. No. 188,435, Apr. 29, 1988, Pat. No. 4,961,735.

[51] Int. Cl.$^5$ .................. A61F 13/16; A61L 15/00
[52] U.S. Cl. .................. 604/378; 604/371; 128/156
[58] Field of Search .............. 128/155, 156; 604/371, 604/378, 384

[56] References Cited

U.S. PATENT DOCUMENTS

| | | | |
|---|---|---|---|
| Re. 28,674 | 1/1976 | Guyette | 604/371 |
| 2,254,883 | 9/1941 | Boyle | 128/156 |
| 2,841,529 | 7/1958 | Schmidt et al. | 128/155 |
| 3,063,452 | 11/1962 | Guercio | 604/378 |
| 3,561,441 | 2/1971 | Lombardi | 128/156 |
| 3,654,929 | 4/1972 | Nilsson et al. | 604/378 |
| 3,658,065 | 4/1972 | Hirsch | 128/156 |
| 3,709,221 | 1/1973 | Riely | 128/156 |
| 3,811,445 | 5/1974 | Dostal | 604/384 |
| 3,930,498 | 1/1976 | Monnet et al. | 128/156 |
| 3,976,075 | 8/1976 | Chinai et al. | 604/371 |
| 4,072,150 | 2/1978 | Glassman | 604/378 |
| 4,214,582 | 7/1980 | Patel | 128/156 |
| 4,414,268 | 11/1983 | Baldwin | 604/356 |
| 4,502,156 | 3/1985 | Wishman | 604/378 |
| 4,714,466 | 12/1987 | Dohzono et al. | 604/378 |
| 4,961,735 | 10/1990 | Siciliano | 604/378 |

*Primary Examiner*—C. Fred Rosenbaum
*Assistant Examiner*—Sharon Finkel
*Attorney, Agent, or Firm*—Rosen, Dainow & Jacobs

[57] ABSTRACT

The present invention relates to a system for containing and draining fluids comprising a two layered evaporating bandage used in combination with an absorptive means which system will drain and dry harmful body fluids from surgical incisions, wounds and burns.

20 Claims, 1 Drawing Sheet

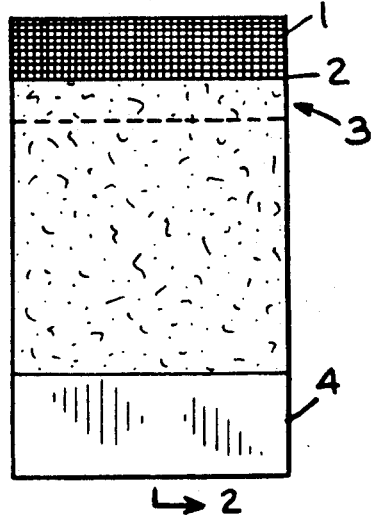
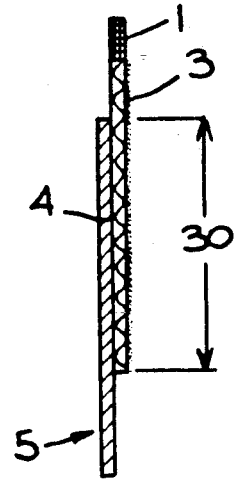
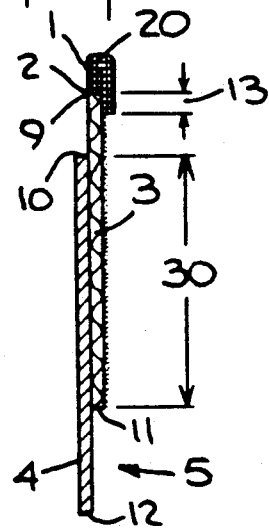
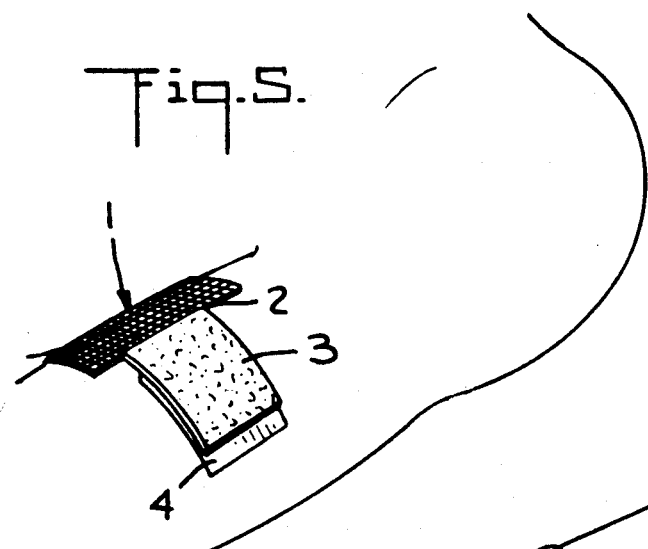
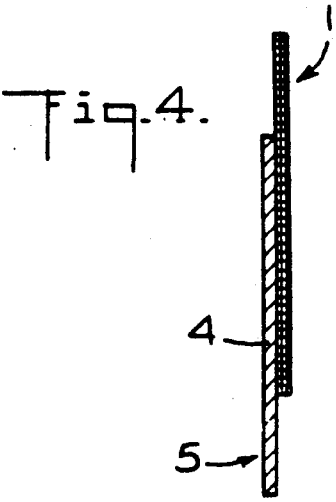
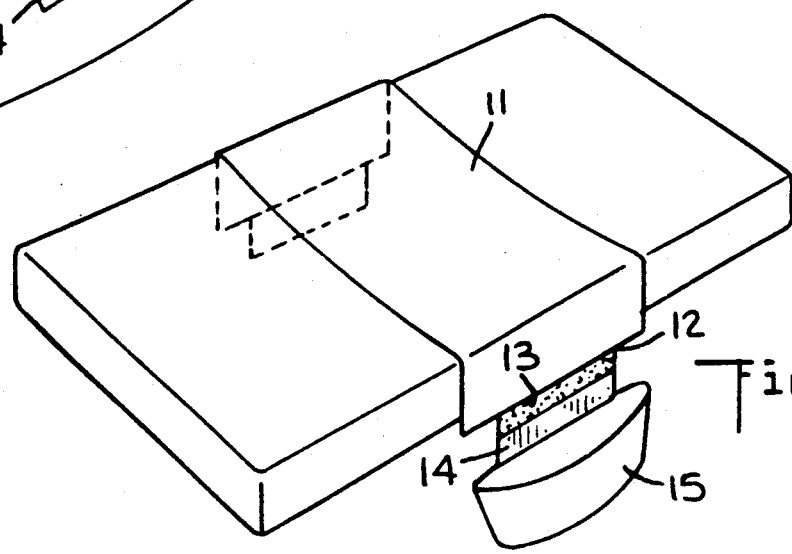

EVAPORATING ATTACHMENT MEANS SUITABLE FOR CONTAINING AND DRAINING FLUIDS EMANATING FROM A SUBJECT

This application is a continuation-in-part of U.S. patent application No. 07/188,435, filed Apr. 29, 1988, now U.S. Pat. No. 4,961,735.

BACKGROUND OF THE INVENTION

The present invention relates to an article comprising a staggered layering of an absorbent material over a non-absorbent material which absorbs, drains, siphons, controls and evaporates body fluids which emanate from surgical incisions, wounds and burns—as well as other types of body fluids (urine, perspiration)—which contribute to general discomfort and particularly to discomfort and health problems of bedridden patients, thereby eliminating certain problems associated therewith.

One of the problems associated with certain surgical procedures on a subject, or the treatment of burns sustained by a subject, is the control of fluids emanating from the subject's system which result therefrom. For example, after major surgery, in many instances there is external bleeding which occurs at the wound or incision. The blood flowing from the open source is really a tissue made up of a liquid material containing about 50% by volume of white cells and red cells and platelets. The other half of the volume of blood is made up of a fluid called plasma. In addition to blood emanating from the source, inflammation may set in during the course of healing of the wound or incision whereupon white blood cells are chemically attracted to the damaged area. When large numbers of white cells engulf bacteria and dying cells, they themselves die. In the case of a serious local inflammation in the vicinity of a wound or incision, the dead cells accumulate as pus and ooze from the wound or incision to outside of the body.

In the instance of a burn over a portion of the subject, the fluid generated as a result of the burn oozes from the burn site.

Many of the current gauze bandages and gauze surgical dressings in use today only absorb the fluids from the injured area on the subject. Thus, fluids that soak into these current bandages remain in the gauze fabric. When the bandage is saturated, it must be changed because retention of the fluids in the gauze bandages, in contact with the incision, wound or burn, can lead to serious infection. Furthermore, the presence of the aforementioned fluids in contact with the injured skin delays the healing process.

As a consequence, current gauze bandages are changed frequently. The procedure involved in changing a bandage saturated with fluids from the subject during the healing process may reverse to some degree whatever healing that has taken place.

In the case of bedridden patients, profuse perspiration and incontinence lead to discomfort as well as hygiene and health problems, particularly bed sores.

Often hospitals, veterinary clinics and/or nursing homes (and bedridden patients wherever they may be) utilize a protective pad that lies directly beneath the subject. Its function is to absorb and contain urine, perspiration, etc., so that these fluids do not saturate and soil the bedding.

SUMMARY OF THE INVENTION

Evaporating Bandaging Attachment Mode

The present invention relates generally to a system for containing and draining fluids emanating from a subject comprising absorptive means in combination with evaporative means and means to affix said evaporative means to said absorptive means, said evaporative means comprising a first layer made of a moisture-absorbent material and a second layer made of a non-moisture absorbent material; said first and second layers having top and bottom edge portions which are aligned and secured in staggered positions relative to each other so that at one end, said first layer top edge portion extends beyond the second layer top edge portion thereof and is in contact with said absorptive means, said absorptive means, said absorptive means being situated in contact with an area of the subject from which a fluid is emanating, the top edge portion of said first layer of said evaporative means being attached to the bottom edge of said absorptive means and positioned in a vertical plane below said bottom edge of said absorptive means, and, correspondingly, said second layer bottom edge portion of said absorptive means extends beyond the said first bottom edge portion at the other end thereof, there being a resulting area wherein the back surface of the lower portion of said first layer is in direct overlapping contact with the front surface of the upper portion of said second layer. Alternatively, the absorptive means and the first layer of the evaporative means may comprise a single continuous sheet of absorbent material with said second layer being affixed to and extending below the back of the lower portion of the continuous sheet. Finally, for certain embodiments there is provided means for collecting the fluids which have traveled via gravity from said absorptive means and said evaporative means.

One specific embodiment of the system of the present invention involves an evaporating bandage attachment. The attachment used in the system comprises a staggered layering of an absorbent material over a nonabsorbent material and is adapted to be attached to the edge of a bandage (e.g., gauze) which is applied to cover an area on the subject which contains an incision, wound or burn and to absorb the fluids which emanate therefrom. The bandage mode of the present invention, which for the sake of convenience is referred to herein as "an evaporating bandage attachment," drains, contains, evaporates and dries potentially harmful fluids which emanate from injured skin from two to five times faster than current gauze bandaging used alone. This unexpected benefit in evaporation and drying is a result of the evaporating bandage attachment construction which consists of the aforementioned staggered layering of an absorbent material over a nonabsorbent material.

Mattress Pad Mode

Another specific embodiment of the system of the present invention is a mattress pad evaporative attachment. This attachment also features a staggered layer of highly absorbent nonwoven material over a nonabsorbent material, which is attached to the lower edge of an absorptive means, generally a protective pad such as a mattress pad placed beneath the subject. The nonwoven absorbent material used in the mattress pad evaporative attachment possesses superior "wicking" properties, i.e., by some type of capillary-like action the nonwoven material transports the moisture, etc. away from the skin. This wicking action draws the fluids in question to the edge of the nonwoven absorbent material, thus lessening the fluid saturation directly beneath the subject.

An unexpected benefit of the present invention when utilized in the mattress pad attachment embodiment is its ability to virtually siphon and drain liquids quickly away from the source. When the evaporating system of the instant invention is applied to the wicking nonwoven materials currently used in mattress pads, it was determined that the instant evaporating system drained and dried liquids 10 to 14 times faster than when no siphoning/draining action was applied to the identical absorbent/wicking mattress pad materials.

The preferred embodiment of the system using the mattress pad attachment is to secure the top edge of the absorptive layer of the evaporative means to the lower edge of the absorbent pad means, thereby suspending the evaporative means in a plane below the edge of the absorbent means. Immediately below the evaporative means is placed a collecting means such as a bag, pail, etc. to collect the fluids passing through the evaporative means. In this configuration, the evaporating system functions in a manner to provide a siphon-like action thus allowing the aforementioned collecting means, such as the flexible pouch or bag noted to be placed beneath the evaporating means to collect body fluids that have been drained from the subject.

BRIEF DESCRIPTION OF THE DRAWINGS

While the specification concludes with claims particularly pointing out and distinctly claiming the subject matter of the invention, it is believed the invention will be better understood from the following description taken in conjunction with the accompanying drawings, wherein:

FIG. 1 illustrates a front view of one embodiment of the bandage attachment;

FIG. 2 shows a cross sectional view of the bandage attachment of FIG. 1 in place on the body;

FIG. 3 shows a more detailed cross sectional view of the bandage attachment of FIG. 1;

FIG. 4 shows an alternative embodiment of the invention wherein the first layer of the evaporative portion of the system is a continuation of the absorptive material in contact with the subject.

FIG. 5 shows the bandage attachment in place on the body; and

FIG. 6 shows an oblique front view of the mattress pad attachment embodiment of the present invention.

The preferred bandage attachment configuration of the present invention is depicted in FIG. 1.

Gauze bandage 1 covers the injured area of the subject. The lower edge of same is attached to and is in direct contact with top edge 2 of the absorbent layer portion 3 of the absorbent layer portion of the evaporating attachment. Layer portion 3 comprises entirely an absorbent material capable of being sterilized. The absorbent layer 3 absorbs from the gauze material (1) fluids oozing from the wound or burn. The material comprising the absorbent layer 3 is preferably fabricated from a highly absorbent non-woven material; however, an additional material such as terry cloth, i.e., a cotton material which contains a looped pile construction can also be used. If terry cloth is used, instead of the preferred nonwoven material, the preferred actual construction of layer 3 is an absorbent material comprising a terry pile surface on the distal side (i.e., the side facing the source of the body fluid) and a ribbed or plain knit surface on the proximal side.

The front view of FIG. 1 shows layer 3 as the upper absorbent layer comprising the absorbent materials described above as being in front of or, depending upon the perspective, on top of the seoncd layer 4. Accordingly, the distal or back side of absorbent layer 3 is secured in overlapping contact with a proximal or front portion of a portion of a layer of nonabsorbent material 4. Only a portion of layer 4 is located directly adjacent to layer 3, as the remaining portion of layer 4 is located beneath the absorbent layer 3. Referring then to FIG. 2, it can be seen that there are two distinct layers of different materials beneath absorbent gauze 1, one atop and in front of the other, which are depicted at mid-section 30. Bottom section 5 of the bandage attachment consists of a continuation of the nonabsorbent material layer 4 that extends beyond the bottom edge of the absorbent layer 3.

The invention depicted in FIGS. 1 and 2 relates to the use of the bandage attachment shown, which provides an efficient system of containing and draining fluids emanating from a subject using said evaporative bandage attachment. The system comprises contacting the location on the subject from which said fluids are emanating with the gauze bandage to which the duel layered article is secured as depicted in FIGS. 1 and 2.

A more detailed depiction of the invention is shown in FIG. 3, evaporative means 1 comprising a first (upper) 3 and second (lower) 4 layers have top (9, 10) and bottom (11, 12) edge portions respectively which are aligned and secured in staggered positions relative to each other so that at one end, said first layer top edge portion (9) extends beyond the second layer top edge portion (10) thereof and is in contact at area (13) with the gauze bandage 20 situated at a location on the body from which said fluids are emanating, and, correspondingly, said second layer bottom edge portion (12) extends beyond the said first bottom edge portion (11) at the other end thereof, there being a resulting area (30) not in contact with the edge of the gauze bandage 20 from which said body fluids are emanating, wherein the portion of the surface of the lower portion of said first layer 3 is in direct contact with a portion of the surface of the upper portion of said second layer 4.

As noted above and depicted in FIG. 3, top section 1 (above section 30) can be comprised of swatches of different absorbable materials suitable for bandaging wounds, burns, sweat, etc. Top layer 3 made of a nonwoven fabric is secured at 2 at its edge to the gauze bandage. The gauze section 20 can be secured to the terry cloth section 3 along the respective edges in section 13 by any suitable means contiguously or by an overlapping arrangement as shown, wherein the top edge of the absorbent layer is attached to the bottom edge of the bandage.

Although reference is made consistently herein to gauze as the material comprising the absorbent layer, this is done by way of illustration as any suitable material capable of absorbing the fluids emanating from the subject can be used. This is especially the case in the embodiment depicted in FIG. 4 where a single continuous sheet of material is used which performs two functions.

FIG. 4 shows an alternative embodiment of the articles depicted in FIGS. 1-3 wherein the layer 1 in contact with the subject is a continuous sheet of absorbent material which also serves as the first layer of the evaporative system in contact with and secured to non-absorptive layer 4.

FIG. 5 shows the bandage of the present invention in place on the upper arm of a person in a supine position. The bandage is draped so that the nonabsorptive portion is pointed downward toward the ground.

The system evaporating bandage attachment must be applied to the wound or burn area in such a manner as shown in FIG. 5 that the bandage section 1 is attached at 2 to attachment 3, so that the system drapes over the body and points downward as much as possible toward the ground. This allows the effect of gravity to influence migration of the body fluids flowing onto the evaporating bandage.

The capillary action of the body fluids collected, absorbed and retained in the absorbent material of the evaporating bandage, in conjunction with the force of gravity, draws the fluids down from bandage 1 into layer 3. Since layer (3) has an adjacent layer (4) of a nonabsorbent material, there is a resistance to absorption from behind section 3. Since the bottom of layer 3 borders on the non-absorbing material of section 5, absorption is also resisted from below layer 3. This dual resistance of absorption from both behind and below creates a reservoir like effect in layer 3.

Fluids flowing from a body wound or incision may be set in motion by an osmotic pressure type phenomenon supplemented by gravity acting in conjunction with the capillary movement through the absorbent material. The simplest path for the moving fluids contained within the bandage is the path of evaporation.

FIG. 6 depicts the mattress pad made of the present invention. This embodiment comprises an absorbent mattress pad (11) having a non-absorbable backing on it, such as polyethylene or polypropylene (not shown), draped over the mattress on the bed. The slight indentation of the mattress, resulting from the weight of the subject, is depicted in FIG. 6. On one or both sides of the mattress pad the attachment, comprising absorbent layer 13 and nonabsorbent layer 14, is affixed at 12 using any suitable means.

Collecting means 15 is positioned beneath the attachment to collect the fluids which have traveled through the system.

It has been established that this system works equally well regardless of whether the subject is a human or an animal.

EXAMPLE 1

An initial comparative test was run to establish the efficacy of the evaporating bandage of the present invention. In order to simulate body fluids, 5 ounces of non-dairy creamer were dissolved in 10 ounces of coffee, having a temperature of about 98.6° F. The resultant solution possessed a viscosity within the range of human blood. The solution was gradually dispensed through an eye dropper (to simulate body fluids oozing from injured skin) onto a bandage having an absorbent layer of spun cotton positioned to overlap and in a staggered relationship with a second layer of nylon. The solution was applied to the top edge of the spun cotton layer. A control bandage of spun cotton having the same dimensions was prepared and saturated. Evaporation of the fluid contained by the bandage of the present invention in the experiment was seven times faster than found in the cotton bandage of the prior art.

EXAMPLE 2

Another comparative test was run to establish the efficacy of the evaporating bandage of the present invention. In order to simulate body fluids, a mixture of three tablespoons of non-dairy creamer were dissolved in eight ounces of coffee, having a temperature of about 98.6° F. The resultant solution possessed a viscosity substantially greater than the viscosity range of human blood. A test bandage (A) comprising an evaporating bandage of the present invention measuring 3¼ inches by 2¾ inches by 3/16 inch was fabricated using a sterilized terry cloth and a ribbed nylon strip fastened thereto in such a manner that the terry cloth strip and nylon strip were in staggered, contacting relationship with each other. The sample was mounted on a test stand in a vertical position. A control bandage (B) made of a standard gauze material, measuring 3¼ inches by 2¾ inches by 3/16 inch, was similarly mounted on the test stand. Using a medicine dropper that dispenses drops equal to 1/16 of a millileter, one drop of liquid was applied to the top edge of test bandage A and control B every three seconds. After 8.75 ml, the control bandage became saturated and could no longer contain the liquid being applied and, thereafter, evidenced considerable leakage therefrom when further liquid was applied.

In contrast, the evaporating test bandage of the present invention 8 held 25 ml without evidencing any leakage. The test demonstrates the greater ability of the evaporating bandage of the present invention compared with the prior art, to contain profuse oozing of body fluids when in place over an incision, wound or burn. This greater containment capacity will decrease the frequency of bandage changes in those situations where the skin is severely injured.

EXAMPLE 3

A comparative test was run wherein 2.5 ml of tap water was applied at room temperature to an evaporating bandage test sample which measured 3¼ inches by 2¼ inches by ⅛ inch and also to a control gauze bandage having the same dimensions. Both bandages were mounted in a vertical position. The tap water was applied to the top edges of the test and control bandages at the rate of one drop every three seconds. The evaporative test bandage was dry to the touch 25 minutes after the 2.5 ml of water was supplied. The control sample bandage was dry 135 minutes after the 2.5 ml of water was applied.

EXAMPLE 4

This test was conducted using samples having the identical dimensions, along with test amounts and procedures as set forth in Example 3 above; however, both the test and control bandages were inclined at an angle of approximately 30° from vertical to simulate bandages draped on the human body so that a portion of the bandage will tilt at an angle and be pointing toward the ground. The test stand containing the samples was placed in a room having a temperature of 71° F. with no air movement. Test B was dry 65 minutes after the 2.5 ml of water was applied. The control sample B was not dry until 155 minutes after the 2.5 ml of water was applied.

EXAMPLE 5

The procedure used in Example 3 above was duplicated with the exception that the control sample placed in a horizontal position, i.e., perpendicular to the vertical plane. The water was applied to one edge of the sample. The control bandage was not dry until 220 minutes after the 2.5 ml of water was applied. This test is closer to the realistic occurrences when gauze bandaging is applied to a person who is bedridden, as the bandaging would be lying flat upon the skin of the patient.

EXAMPLE 6

The following comparative test was conducted to demonstrate the accelerated siphoning action of the present invention.

Two strips (A and B) were cut from an absorbent/wicking non-woven material comprising an evaporating bandage suitable for draining and drying body fluids. Both strips were 13 inches long and 13 inches wide. Test strip "A" then had a B inch length of a plastic coated adhesive taped to each end. The tape was 1B inches wide and was applied so it came ⅛th inch below the edge of absorbent strip A. The identical taping procedure was applied to both ends of 13 inch absorbent strip B.

The taping of the absorbent strip in this fashion accommodates one element of the evaporating system of the current invention, i.e., the staggered layering of an absorbent material over a nonabsorbent material.

A bowl 5 inches in diameter at the top edge was filled with 1 ounce of water. The top edge of the bowl had a 2 inch rise from the base of the bowl. The 1 ounce of water had a depth of ⅜ inches when placed in the bowl.

Test strip "A" was placed in the bowl so that its center was in the center of the bowl, thus allowing each end of the strip to hang over the edge of the bowl. Each edge was hanging a perpendicular length of 3B inches from the edge of the bowl.

These test conditions simulate one of the conditions when a patent is lying in bed. The patient's weight will cause an indentation in the mattress. This means that any liquid beneath a patient on for example, an incontinent pad, will have to be wicked up on an incline.

Test strip "A" drained the 1 ounce of water from the bottom of the bowl in 24 minutes. While there was still some dampness in the strip, there was no residue of liquid in the bottom surface of the bowl.

Control strip "B" (identical to Test Strip "A" except it had no plastic coated adhesive tape on its edges) was placed in 1 ounce of water in a bowl identical to the one used for test strip "A." The edges of control strip "B" hung over the bowl in the exact manner as test strip "A" edges hung over its bowl. Control strip "B" drained the 1 ounce of water from the bowl in 48 minutes.

These tests demonstrate that an absorbent/wicking fabric can siphon liquids. Since the edges of both the "A" and "B" strips were at a lower point than the base of the bowl, this satisfied the key element in a siphoning system, namely, that the exit end of a siphoning apparatus has to be lower than the entrance end so that gravity can act on capillary movement.

EXAMPLE 7

An additional test was conducted to establish that the liquids were moved out of the bowl mainly by a siphoning force.

Test Strip "A" was placed in a bowl of liquid in such a way so that one edge was hanging below the base of the bowl and so that the other edge was hanging slightly above the base of the bowl. The lower hanging edge had a continuous dripping of liquid over an observed 10 minute period. The other edge had no dripping over the same observed 10 minute period.

The identical test was performed on Control Strip "B," and the results were identical. The lower edge of the "B" strip had a continuous dripping while the other edge had no dripping.

The aforementioned tests demonstrate that the evaporating system of the present invention approximately doubles the siphoning force of absorbent/wicking materials.

In the foregoing specification, the presently preferred embodiments of the invention are described; however, it will be understood that the invention can be otherwise embodied within the scope of the following claims.

I claim:

1. A system for containing and draining fluids emanating from a subject comprising absorptive means in combination with evaporative means and means to affix said evaporative means to said absorptive means, said evaporative means comprising a first layer made of a moisture-absorbent material and a second layer made of a non-moisture absorbent material; said first and second layers having top and bottom edge portions which are aligned and secured in staggered positions relative to each other so that at one end, said first layer top edge portion extends beyond the second layer top edge portion thereof, and said first layer top edge portion is in contact with a lower edge of said absorptive means, said absorptive means being situated in contact with an area of the subject from which a fluid is emanating, said evaporative means being positioned in a vertical plane below said edge of said absorptive means; and, correspondingly, said second layer bottom edge portion of said evaporative means extends beyond said first bottom edge portion at the other end thereof, there being a resulting area wherein the top surface of the lower portion of said first layer is in direct contact with the bottom surface of the upper portion of said second layer.

2. The system defined in claim 1 wherein said absorptive means and said first layer of moisture-absorbent material comprise a single continuous sheet of material.

3. The system defined in claim 1 which contains means for collecting the fluids which have traveled via gravity from said absorptive means and said evaporative means.

4. The system defined in claim 1 wherein said absorptive means is a bandage comprising a woven or nonwoven fabric.

5. The system defined in claim 1 wherein said absorptive means is a mattress pad having a woven or nonwoven fabric upper layer adhered to a moisture impermeable layer.

6. The system defined in claim 1 wherein the first layer is made of a non-moisture-absorbent material comprising a polyamide.

7. The system defined in claim 1 wherein the first layer is made of a moisture-absorbent material comprising wool.

8. The system defined in claim 1 wherein the first layer is made of a moisture-absorbent material comprising cotton and the second layer is made of a nonmoisture-absorbent material comprising a polyamide.

9. The system defined in claim 5 wherein said nonwoven fabric is hydrophilic polypropylene.

10. The system defined in claim 5 wherein said cotton is terry cloth.

11. The system defined in claim 4 wherein said bandage is nonwoven polypropylene and secured to said lower edge of absorptive means made of a nonwoven polypropylene fabric having a polyethylene film backing.

12. The system defined in claim 5 wherein said cotton comprises a first layer made of terry cloth secured to said lower edge of absorptive means made of gauze.

13. The system of claim 9 wherein said non-moisture absorbent material comprises a polyamide material.

14. The system of claim 12 wherein said non-moisture absorbent material comprises a polyamide material.

15. The system defined in claim 1 wherein the first layer of a moisture absorbent material is made of a highly hydrophilic nonwoven material with extreme wicking ability and the second layer made of a nonmoisture absorbent material.

16. The system defined in claim 15 wherein said first layer of a hydrophilic nonwoven material contains a second section made of gauze.

17. The system of claim 15 wherein said non-moisture absorbent material comprises a plastic coated adhesive tape.

18. The system of claim 4 wherein said non-moisture absorbent material comprises a plastic coated adhesive tape.

19. The system defined in claim 4 wherein the first layer of a moisture absorbent material is made of a highly hydrophilic nonwoven material with extreme wicking ability and the second layer made of a nonmoisture absorbent material.

20. The system defined in claim 1 wherein the first layer is made of a moisture-absorbent material comprising cotton.

* * * * *